United States Patent [19]

Genatempo et al.

[11] 4,440,207
[45] Apr. 3, 1984

[54] ANTIBACTERIAL PROTECTIVE CAP FOR CONNECTORS

[75] Inventors: Vince Genatempo, Lake Geneva, Wis.; Frank Karrasch, Wadsworth, Ill.

[73] Assignee: Baxter Travenol Laboratories, Inc., Deerfield, Ill.

[21] Appl. No.: 378,315

[22] Filed: May 14, 1982

[51] Int. Cl.³ ............................................. A61M 5/14
[52] U.S. Cl. .................................. 150/52 R; 206/206; 206/207; 604/256; 604/905
[58] Field of Search ...................................... 604/27–29, 604/265, 280, 283, 93, 256, 905, 187, 192, 198, 263; 215/228, DIG. 3; 150/52 R; 206/206, 207

[56] References Cited

U.S. PATENT DOCUMENTS

| | | | |
|---|---|---|---|
| 3,396,727 | 8/1968 | Mount | 604/265 X |
| 4,232,677 | 11/1980 | Leibinsohn | 604/265 X |
| 4,273,247 | 6/1981 | Earls | 215/228 |
| 4,306,976 | 12/1981 | Bazzato | 604/28 X |
| 4,340,052 | 7/1982 | Dennehey | 604/905 X |
| 4,354,490 | 10/1982 | Rogers | 604/905 X |
| 4,403,992 | 9/1983 | Bertellini et al. | 604/29 |

OTHER PUBLICATIONS

*Dialysis & Transplantation* 10 (May 1981): 421, Quinton Instrument Co., advertisement for their product BETA CAP II ™.
"The BETA CAP ™ System" advertising brochure, Quinton Instrument Co. (undated).

*Primary Examiner*—C. Fred Rosenbaum
*Assistant Examiner*—Michelle N. Lester
*Attorney, Agent, or Firm*—Paul C. Flattery; Garrettson Ellis; Thomas A. Kmiotek

[57] ABSTRACT

An article of manufacture and a method are provided where a protective cap for a connector provides antibacterial effect to the connector by fixedly lining a chamber of the protective cap with an absorbent material retaining an antiseptic. By mating a skirt on the protective cap with a corresponding flange on a medical connector, a contamination proof seal is also provided which functions to limit contamination from the outside of the cap and retain a liquid antiseptic on the inside of the cap.

15 Claims, 3 Drawing Figures

ANTIBACTERIAL PROTECTIVE CAP FOR CONNECTORS

FIELD OF THE INVENTION

This invention relates to protective caps for medical connectors or ports and to closure systems for the ends of medical tubing or for ports on medical apparatus. The invention particularly relates to a protective cap for a medical connector or medical port opening which provides an antibacterial effect. An improvement of the present invention lies in reliably providing an antibacterial effect to a connector or port opening.

BACKGROUND OF THE INVENTION

Typical medical connectors in wide use are connectors for solution containers, administration sets and catheters. Medical procedures require a connection where the bioburden (i.e. bacterial population) is minimized. Protective caps containing an antibacterial agent can reduce the bioburden by providing a bacteriocidal or bacteriostatic effect to connector sites prior to use. A protective cap having an antibacterial effect is particularly desirable for components used in peritoneal dialysis, for example CAPD.

At the present time thousands of patients who have limited or nonexistent kidney function due to end state renal disease are being maintained by CAPD, and other forms of peritoneal dialysis.

In the CAPD procedure, connections between dialysis solution containers and administration sets which communicate with the peritoneal catheter must be made and broken, normally several times a day. Particularly when the patient is doing his own CAPD exchanges, there is the possibility that the sterility of the flow path between the various solution containers and the peritoneal cavity may be compromised. Airborne bacteria or the accidental contamination of an open connector by the patient can contaminate the flow path. The result of such a contamination can be peritonitis.

It is desirable to provide a protective cap for medical connectors such as CAPD connectors in particular, which securely receive and provide an antibacterial effect to the connector. For example, the Quinton Cap manufactured by Quinton Instrument Co., is sold, which contains liquid antiseptic such as povidone iodine freely flowing within the cap in its mode of use, to bathe the connector in antiseptic. However, this sytem requires filling of the system with antiseptic at the time of use, and thus involves a time-consuming process with the added disadvantage that the antiseptic can be spilled.

BRIEF SUMMARY OF THE INVENTION

The present invention provides a protective cap for a connector which securely receives and provides an antibacterial effect to the connector. At least a portion of the protective cap interior is lined with an absorbent material which retains an antiseptic. A connector covered by the protective cap is thus placed in an antibacterial environment made possible by contact of the connector with the antiseptic-retaining absorbent material, or from migration of the antiseptic, or both.

The protective cap of this invention is presently contemplated for use on solution container connectors, and particularly connectors communicating with the patient in peritoneal dialysis procedures. The liquid antiseptic such as povidone iodine, retained in the absorbent material lining within the cap, provides the antibacterial effect. However, use of the protective cap of this invention is by no means limited to the field of peritoneal dialysis. The protective cap of this invention may also be used for other medical applications or other procedures where it is desired to provide an antibacterial connection.

The protective cap of this invention is designed to securely receive a connector. The cap itself has a first, outer chamber which has an external opening defined by a skirt which allows engagement with a connector. An absorbent material lines the outer chamber and is affixed therein. The absorbent material retains an antiseptic which may be a liquid such as povidone iodine.

A second, inner chamber transversely smaller than the first chamber is positioned adjacent and open to the first chamber. The second chamber is designed to connect and receive the medical connector, the end of an administration set, or other types of tubes or ports. Internal threads are defined in the second chamber, and are designed to engage with external threads of a connector, to provide a threaded connection between the connector and cap. A flange on the connector may be received within the skirt of the protective cap to provide a seal, which additionally helps to reduce the possibility of contamination of the connector.

In manufacturing the cap, the first, outer chamber of a protective cap may be lined with the absorbent material. Ribs formed in the first chamber and directed towards the center of the first chamber project into the absorbent material and act as energy directing ribs, focusing ultrasonic energy to the absorbent material during an ultrasonic sealing step, whereby the absorbent material may be firmly welded to the inner chamber of the protective cap. Thereafter, an antiseptic is provided to the absorbent material, which takes it up and retains it.

BRIEF DESCRIPTION OF THE DRAWINGS

For a more complete understanding of this invention, reference should now be had to the embodiment illustrated in greater detail in the accompanying drawings.

In the drawings.

DESCRIPTION OF THE PREFERRED EMBODIMENTS

Figure 1:
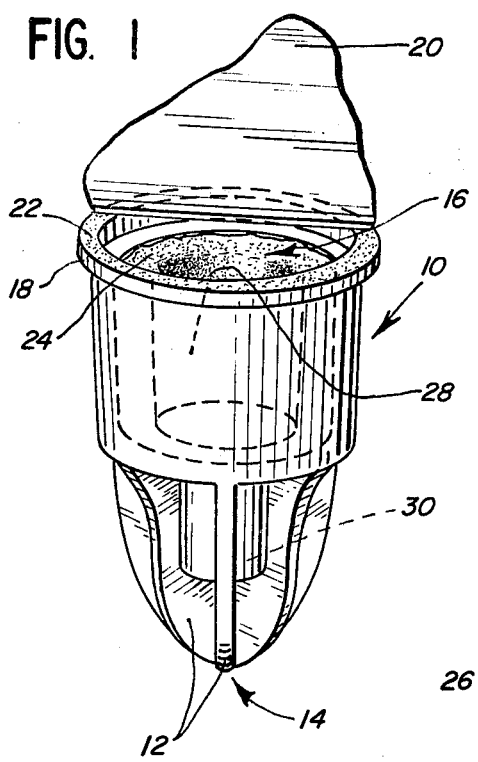
FIG. 1 is a perspective view of the protective cap of this invention.

Turning now to the drawings, FIG. 1 is a perspective view of the protective cap 10 of this invention. Gripping fins 12 on the exterior portion of closed end 14 of protective cap 10 provide a convenient gripping surface.

External opening 16 of cap 10 is defined by skirt 18, which also defines outer chamber 28. A removable water vapor barrier such as peelable lid 20 of known design adheres to outer face 22 of skirt 18, and is shown in the partially open position. Absorbent material 24 lines protective cap 10 and is fixedly attached to the inside of the protective cap.

When removable water vapor, microbial barrier lid 20 is closed, it completely covers and adheres to outer face 22 of skirt 18. Thus when absorbent material 24 retains a volatile antibacterial agent, such as povidone iodine, loss by evaporation is greatly reduced. Alternatively, protective cap 10 may be placed in a preformed plastic blister which is covered by a removable water vapor barrier lid.

Figure 3:
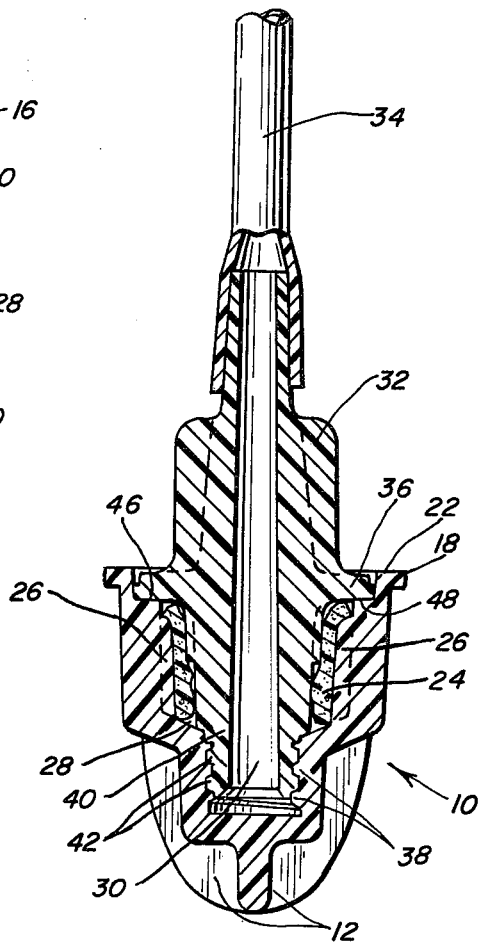
FIG. 3 is a longitudinal cross sectional view of a connector covered by the protective cap of this invention.
Figure 2:
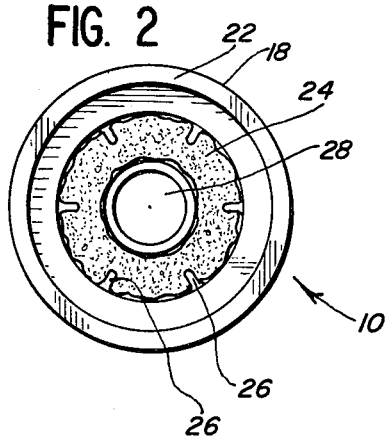
FIG. 2 is an end elevational view of the protective cap of this invention, showing the absorbent material lining and a series of inwardly directed ribs.

The end view of cap 10, as shown in FIG. 2, discloses a series of longitudinally positioned, inwardly directed ribs 26, formed as part of skirt 18. As shown in FIG. 3, inwardly directed ribs 26 are located in first, outer chamber 28 of protective cap 10. Second, inner chamber 30 adjacent, open to outer chamber 28, is also shown.

Referring again to FIG. 2, inwardly directed ribs 26 function as energy directors for ultrasonic welding of absorbent material 24 to the inner wall of skirt 18 (FIG. 3). The cap wall, including ribs 26, is preferably made of a thermoplastic material that will weld to the thermoplastic of absorbent material 24 when exposed to ultrasound energy. Absorbent material 24 is filled with an antiseptic after welding. Preferably, the wall of protective cap 10 is made of Hytrel ®5556 polyester manufactured by E. I. du Pont de Nemours & Co., and absorbent material 24 is made of polyether-based polyurethane, although substantially equivalent materials can also be used. A preferred antibacterial agent or antiseptic is povidone iodine.

Connector 32 is shown engaged by protective cap 10 in FIG. 3. The connector 32 shown is a typical connector used with CAPD tubing sets. Tube 34 is shown extending from connector 32 to communicate, for example, with a Tenckhoff catheter implanted in the peritoneal cavity of a patient.

Skirt 18 of protective cap 10 is shown receiving flange 36 of connector 32. Inner chamber 30 having internal threads 38, cooperates to threadedly lock with external threads 42 of connector 32.

The tube of absorbent material 24 is shown contacting main tubular portion 40 of connector 32. Preferably, absorbent material 24 retains an antiseptic or antibacterial agent. In this manner, an antibacterial effect is provided to main tubular member 40 of connector 32, as well as threads 42 through migration of the antiseptic.

Skirt 18 may be proportioned to form a tight, annular seal area 46 with flange 36. Annular step or shoulder 48 may also be provided in skirt 18 and positioned to engage flange 36 for added sealing, and also to prevent overadvancement of connector 32 into cap 10, which could damage the respective threads 42, 38.

The embodiment illustrated in FIG. 3, including protective cap 10 and connector 32, also comprises the antibacterial closure system of this invention. The closure system is effective in minimizing contamination of a connector before it is used or between uses.

The above has been offered for illustrative purposes and is not intended to limit the invention of this application, which is defined in the claims below.

What is claimed is:

1. A protective cap for a connector which securely receives and provides antibacterial effect to the connector, said cap comprising:
a first outer chamber having an external opening fixedly lined with absorbent material, said absorbent material retaining an antiseptic, said first outer chamber being defined by a skirt proportioned for sealing engagement with the connector; and
a second, inner chamber having a closed inner end, smaller than said first chamber, adjacent and open to said first chamber, having connecting means for receiving connecting means from said connector.

2. The protective cap of claim 1 in which said first chamber has a plurality of inwardly directed ribs which function as energy directors for ultrasonic welding of said absorbant material to said inner chamber.

3. The protective cap of claim 1 wherein said internal connecting means of said second inner chamber comprise internal threads for threaded cooperation with external threads.

4. The protective cap of claim 1 further comprising a plurality of gripping fins on an exterior portion of said protective cap.

5. The protective cap of claim 1 wherein said absorbent material is tube shaped.

6. The protective cap of claim 1 wherein said skirt of said protective cap is proportioned to securely engage a mating flange of a connector received therein.

7. A protective cap for an externally threaded, flanged medical connector which securely receives and provides antibacterial effect to the medical connector, said cap comprising:
a first, outer chamber having an external opening and having a plurality of inwardly directed ribs, an absorbent material lining said inner chamber, carried on the inner surfaces of said ribs, said absorbent material retaining a liquid antiseptic;
a second, inner chamber, smaller than said first chamber and adjacent and open to said first chamber, having internal threads for threaded cooperation with external threads of a connector; and
a skirt defined by said external opening to said first inner chamber for sealingly engaging a flange of a connector received in said cap.

8. The protective cap of claim 7 wherein said absorbent material is made of polyether-based polyurethane and said antiseptic is povidone iodine.

9. The protective cap of claim 7 wherein a removable water vapor barrier lid completely covers said external opening to said first chamber, and adheres to an outer face of said skirt.

10. The protective cap of claim 7 wherein said cap wall is made of polyester.

11. A protective cap for an externally threaded, flanged medical connector which securely receives and provides an antibacterial effect to the medical connector, said cap comprising:
a first, outer chamber having an external opening, a tubular thermoplastic, absorbent sponge, said outer chamber having a plurality of inwardly directed ribs serving as energy directors for ultrasonic welding of said tubular absorbent sponge to the inner surfaces of said ribs, said absorbent sponge carrying liquid antiseptic;
a second, inner chamber, smaller than said first chamber and adjacent and open to said first chamber, having internal threads for threaded cooperation with external threads of a connector;
a skirt defined by said external opening to said first inner chamber for sealingly engaging a flange of a connector received therein; and
a removable water vapor barrier lid covering and adhering to an outer face of said skirt.

12. The protective cap of claim 11 wherein said skirt of said protective cap defines an annular shoulder which engages an annular flange on said connector to form an annular seal area.

13. An antibacterial closure system, said system comprising:
   a protective cap for a connector;
   said connector comprising a main tubular member having external connecting means;
   said protective cap comprising:
   a first, outer chamber having an external opening and fixedly lined with an absorbent material, said absorbent material retaining an antiseptic; and
   a second, inner chamber having a closed end, smaller than said first chamber and adjacent to said first chamber and communicating therewith for receiving said external connecting means of said connector, the external opening of the first inner chamber being defined by a skirt, said connector defining a flange which is sealingly surrounded by said skirt.

14. The antibacterical closure system of claim 13 wherein said first chamber has a plurality of inwardly directed ribs serving as energy directors for ultrasonic welding to said absorbent material to said inner chamber.

15. The antibacterical closure system of claim 13 wherein said external connecting means of said connector comprise external threads, and wherein said internal connecting means of said second inner chamber of said protective cap comprise internal threads for receiving said external threads of said connector.

* * * * *